United States Patent
Linares et al.

(10) Patent No.: US 8,514,377 B2
(45) Date of Patent: *Aug. 20, 2013

(54) DETECTION OF CHEMICAL VAPOR DEPOSITION GROWN DIAMOND

(75) Inventors: Robert C. Linares, Sherborn, MA (US); Patrick J. Doering, Holliston, MA (US)

(73) Assignee: SCIO Diamond Technology Corporation, Greer, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/418,122

(22) Filed: Mar. 12, 2012

(65) Prior Publication Data

US 2012/0170019 A1 Jul. 5, 2012

Related U.S. Application Data

(63) Continuation of application No. 12/463,152, filed on May 8, 2009, now Pat. No. 8,134,694.

(60) Provisional application No. 61/051,854, filed on May 9, 2008.

(51) Int. Cl.
*G01N 21/87* (2006.01)

(52) U.S. Cl.
USPC .......................................................... 356/30

(58) Field of Classification Search
USPC .......................................................... 356/30
See application file for complete search history.

(56) References Cited

U.S. PATENT DOCUMENTS

| | | | |
|---|---|---|---|
| 4,573,761 A | 3/1986 | McLachlan et al. |
| 5,801,819 A | 9/1998 | Spear et al. |
| 5,811,817 A | 9/1998 | Ravich |
| 5,880,504 A | 3/1999 | Smith et al. |
| 6,144,448 A | 11/2000 | Mitoma |
| 7,105,822 B1 | 9/2006 | Beesley |
| 7,800,740 B2 | 9/2010 | Gumpesberger |
| 8,134,694 B2 | 3/2012 | Linares et al. |
| 2010/0026985 A1 | 2/2010 | Linares et al. |
| 2010/0053597 A1 | 3/2010 | Linares et al. |

FOREIGN PATENT DOCUMENTS

| | | |
|---|---|---|
| GB | 2244329 A | 11/1991 |
| WO | WO-02/06797 A1 | 1/2002 |

OTHER PUBLICATIONS

"U.S. Appl. No. 12/463,106, Non Final Office Action mailed Mar. 11, 2011", 7 pgs.
"U.S. Appl. No. 12/463,106, Notice of Allowance mailed Feb. 23, 2012", 7 pgs.
"U.S. Appl. No. 12/463,106, Response filed Sep. 28, 2011 to Non Final Office Action mailed Mar. 11, 2011", 7 pgs.
"U.S. Appl. No. 12/463,152, Non Final Office Action mailed Feb. 25, 2011", 5 pgs.
"U.S. Appl. No. 12/463,152, Notice of Aliowance maiied Nov. 7, 2011", 7 pgs.
"U.S. Appl. No. 12/463,152, Response Filed Aug. 18, 2011 to Non-Final Office Action Received Feb. 25, 2011", 6 pgs.
Wang, Wuyi, et al., "Latest-Generation CVD-Grown Synthetic Diamonds from Apollo Diamond Inc.", Gems & Gemology, Winter 2007, vol. 43, No. 4, (2007), pp. 294-312.

*Primary Examiner* — Kara E Geisel
(74) *Attorney, Agent, or Firm* — Schwegman Lundberg & Woessner, P.A.

(57) ABSTRACT

Diamonds may be identified as grown by the use of chemical vapor deposition. One or more diamonds may be placed on a surface and exposed to short wavelength light. Diamonds that fluoresce red may be identified as grown by the use of chemical vapor deposition. In some embodiments, the diamonds are cooled prior to exposure to the short wavelength light.

20 Claims, 2 Drawing Sheets

US 8,514,377 B2

DETECTION OF CHEMICAL VAPOR DEPOSITION GROWN DIAMOND

CLAIM OF PRIORITY

This application is a continuation of and claims the benefit of priority under 35 U.S.C. §120 to Robert C. Linares et al., U.S. patent application Ser. No. 12/463,152, entitled "DETECTION OF CHEMICAL VAPOR DEPOSITION GROWN DIAMOND," filed on May 8, 2009, which claims the benefit of priority under 35 U.S.C. §119(e) to U.S. Provisional Patent Application Ser. No. 61/051,854, filed on May 9, 2008, the benefit of priority of each of which is claimed hereby, and each of which are incorporated by reference herein in its entirety.

BACKGROUND

Chemical vapor deposition (CVD) grown diamonds can be difficult to distinguish from mined diamonds using conventional techniques. Detection of CVD diamond is of importance to the diamond industry to prevent the fraudulent sale of CVD diamond as natural diamond, and to enable the detection of CVD diamond for the purpose of ensuring that there is no misrepresenting natural as CVD diamond. Further, the detection of CVD diamond may be useful for protecting intellectual property rights.

The detection of CVD diamond is difficult and laborious due to the fact that multiple instruments are needed. Such instruments are used to first determine that the diamond in question is a type II A. Colorless cvd diamonds currently are type II A which indicates a very low nitrogen level. The instruments are then used for testing for the presence of N-V centers, which are a substitutional nitrogen atom adjacent to a carbon vacancy. Finally, instruments are used to microscopically view diamonds for features such as strain. All of these tests are required to raise the certainty that a diamond is natural or cvd. None of these tests are complete in themselves, as the presence of N-V centers is rare in natural diamonds, but does occur. Such N-V centers fluoresce at red-orange wavelengths due to it's two main emission peaks centered at 575 and 637 nm. The purer the diamond the weaker the fluorescence. The fluorescence can also be seen by illuminating the diamond with short wavelength ultraviolet light in an expensive instrument such as the "Diamond View". The detection process is long and difficult for large pure stones and nearly impossible for small stones.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
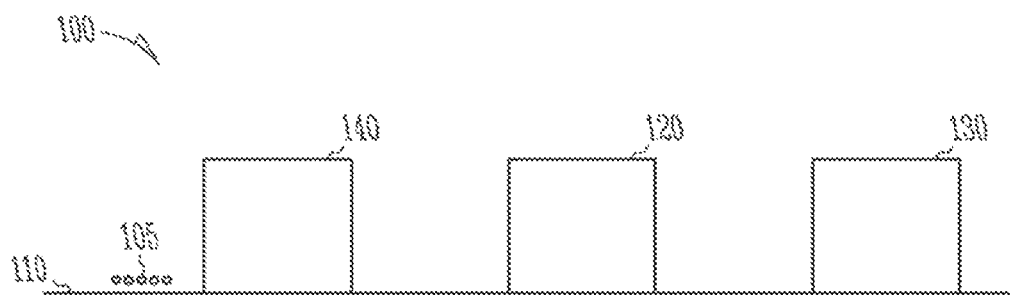
FIG. 1 is a block system diagram illustrating detection of chemical vapor deposition grown diamonds according to an example embodiment.

In one embodiment, a number of cut or uncut diamonds 105 may placed on a platform or a moving belt 110 as illustrated in a system block diagram at 100 in FIG. 1. The entire content of diamond 105 is subjected to short wavelength illumination at a light source 120. In one embodiment, a laser of suitable wavelength may be used as the light source 120. Examples of suitable laser sources include commercially available laser diodes which emit light at wavelengths of 405 nm or 532 nm. Many other wavelengths may be used that cause fluorescence of diamonds with N-V centers, such as wavelengths in the 400 to 550 nm range, and may include portions of the UV range of 10 to 400 nm, or at least the upper portions of the UV range. Other sources that provide suitable wavelength light may also be used.

The CVD diamonds will fluoresce red-orange and may be picked out by hand or by a pick and place robot 130 which is guided to either the fluorescent diamond or the non fluorescent diamond. Alternately, the diamond may be cooled below room temperature as indicated at 140 such as by liquid nitrogen (which greatly increases the brightness of the fluorescence) or some other suitable coolant or thermoelectric cooler. In one embodiment, the diamonds to be tested may be colorless and near colorless. In further embodiments, diamonds of different colors, such as yellow, blue, pink, orange, brown, or other color may be tested.

In this manner, large numbers of diamonds may be inspected to separate the CVD from the natural diamonds. In the event it is desirable to detect and remove diamonds formed by high pressure, high temperature methods, or heat treated natural diamonds, different wavelength filters can be employed in the system to detect these materials by their fluorescence, and such detected materials may be removed by an operator or robotic arm.

Figure 2:
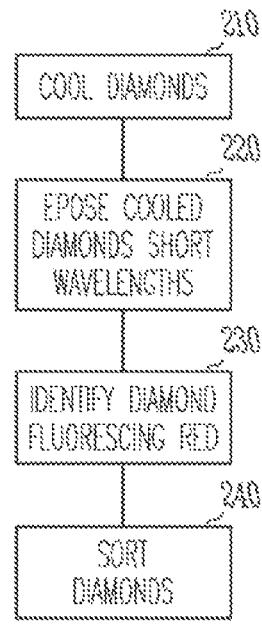
FIG. 2 is a flow chart of a method of detecting chemical vapor deposition grown diamonds according to an example embodiment.

FIG. 2 is a flowchart of a method for sorting natural diamonds from diamonds formed using chemical vapor deposition. At 210, one or more diamonds are cooled below room temperature. The use of liquid nitrogen is one option for cooling, and may be used to cool the diamonds well below room temperature, and in some embodiments, close to the temperature of the liquid nitrogen if desired. At 220, the cooled diamonds are exposed to the short wave length light or radiation. The term short wave length encompasses short visible light in the blue to violet range and at least part of the UV spectrum in one embodiment. In one embodiment, a conveyor belt may be used, and should be run fast enough to ensure that the temperature of the diamonds does not increase significantly from their cooled state. At 230, diamonds that fluoresce red-orange (approximately 780 nm to 585 nm wavelength) may be identified. This may be done by human observation, or by image recognition software and hardware in some embodiments. Thus, a human perceivable attribute, the color of the fluorescence may be used to identify diamonds that are most likely made by CVD processes, without the need for a spectrometer.

At 240, the diamonds may be sorted based on such observation or recognition, either by hand or by some mechanized device. Puffer type devices may be used to blow selected diamonds, either natural or CVD grown diamonds from the conveyor belt as the diamonds move past the puffer or blower. The puffer or blower may be controlled via input from the image recognition software. Diamonds could also be selectively removed using a vacuum pick up tool. The combination of imaging hardware and software along with an automated (robotic) picking tool, and integrating software would allow a fully automated system which identifies and removes the diamonds with red-orange light emission. In such embodiments, the diamonds should be spaced on the conveyer sufficiently to allow the puffer or blower or vacuum pick up tool to selectively remove the diamonds. The process may also be run with human interaction, such as by dipping a quantity of diamond in the liquid nitrogen, spreading them out on a surface, exposing them to the short wavelength light, and picking out the diamonds with a tool by hand. The use of the tool is desired if the diamonds are still at temperatures which could damage skin by contact with the diamonds. In further embodiments, suitable shielding may be provided to protect the operator from harmful UV light.

Some natural diamonds may also have N-V centers that cause fluorescence in response to illumination. It currently appears that such natural diamonds are very rare. The fact that a natural stone has an N-V center or centers may result in a natural stone being classified as a diamond manufactured by CVD methods. In CVD stones, one of the peaks of fluorescence may be a doublet, whereas in natural minded diamond stones, single peaks may be observed. If there is reason to suspect that a natural stone has been mistakenly identified as manufactured, it may be subjected to a higher resolution spectrometer to detect the nature of the peak or peaks. If only single peaks are observed, the diamond may be reclassified as natural. These checks may be performed as part of sort 240 in some embodiments.

Figure 3:
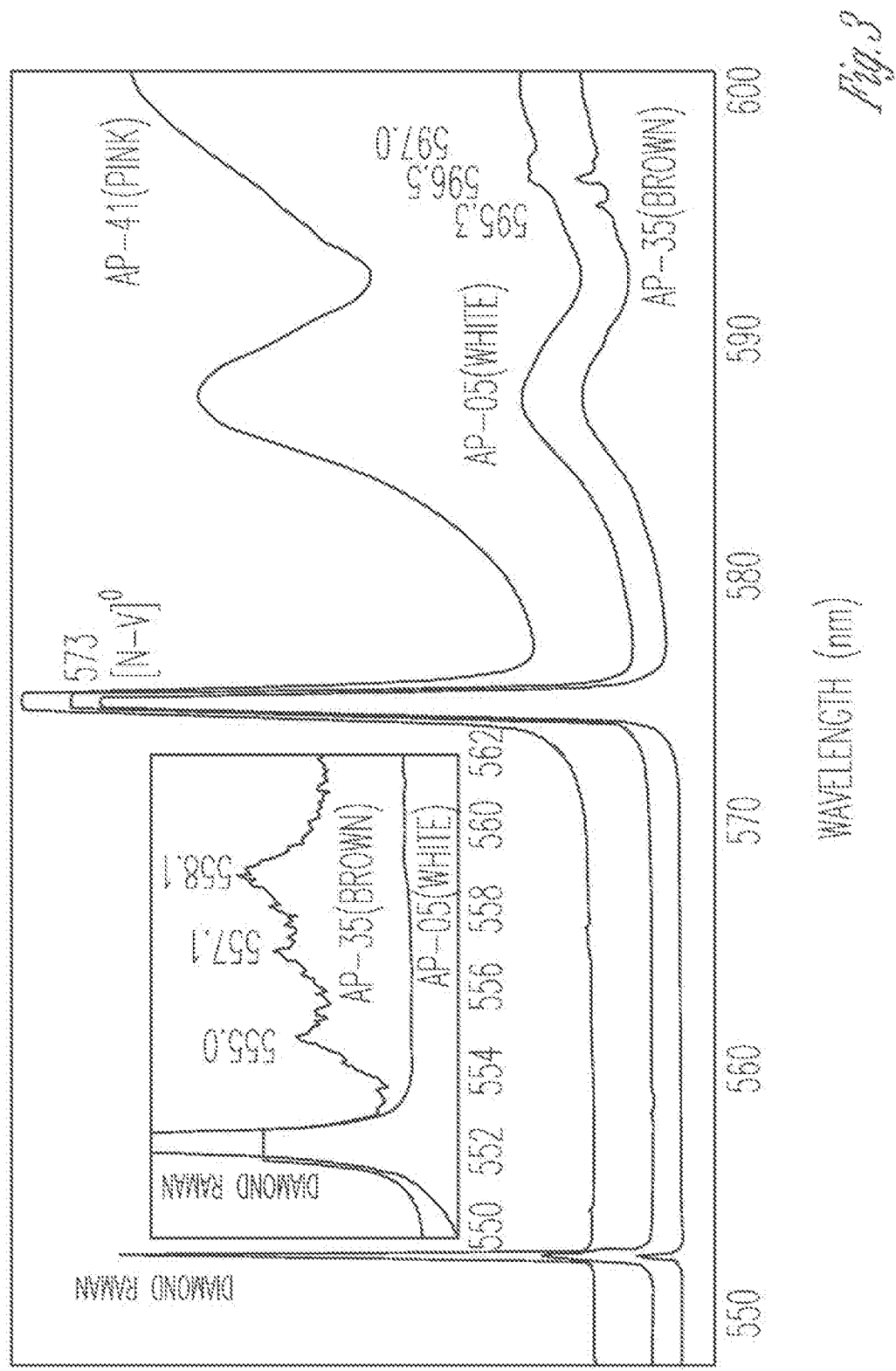
FIG. 3 is a graph illustrating photo luminescence of CVD formed pink, white and brown diamonds.

FIG. 3 is a graph illustrating photo luminescence of CVD formed pink, white and brown diamonds. The same or similar wavelengths can be found using the short ultraviolet and laser light shown above.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A method comprising:
    placing multiple diamonds on a surface;
    cooling the diamonds below room temperature;
    exposing the diamonds to light having a wavelength at or below 550 nm; and
    identifying diamonds that fluoresce between approximately 780 nm to 585 nm.

2. The method of claim 1 wherein the diamonds are cooled by exposing them to liquid nitrogen.

3. The method of claim 2 wherein the cooled diamonds fluoresce at a higher wavelength than uncooled diamonds.

4. The method of claim 1 wherein the surface comprises a conveyor belt.

5. The method of claim 1 wherein the diamonds are cooled by a thermoelectric cooler.

6. The method of claim 1 and further comprising:
    removing the identified diamonds from the surface;
    subjecting the removed diamonds to a spectrometer to detect one or more peaks; and
    classifying diamonds having single peaks as natural diamonds and diamonds having doublet peaks as chemical vapor deposition formed diamonds.

7. A method comprising:
    placing multiple diamonds on a surface;
    cooling the diamonds below room temperature;
    exposing the diamonds to light having a wavelength at or below 550 nm; and
    sorting the diamonds as a function fluorescence between approximately 780 nm to 585 nm.

8. The method of claim 1 and further comprising cooling the diamonds below room temperature prior to exposing the diamonds to light.

9. The method of claim 8 wherein the diamonds are cooled by exposing them to liquid nitrogen.

10. The method of claim 8 wherein the diamonds are cooled by a thermoelectric cooler.

11. The method of claim 7 wherein the surface comprises a conveyor belt.

12. A method comprising:
    placing multiple diamonds on a surface;
    cooling the diamonds significantly below room temperature;
    exposing the diamonds to light having a wavelength at or below 550 nm;
    identifying diamonds that fluoresce between approximately 780 nm to 585 nm as diamonds manufactured using chemical vapor deposition; and
    using a spectrometer to detect doublet emissions when the diamonds are exposed to short wavelength light to confirm that diamonds that fluoresce are manufactured.

13. The method of claim 12 wherein the diamonds are cooled by exposing them to liquid nitrogen.

14. The method of claim 12 wherein the diamonds are cooled by a thermoelectric cooler.

15. The method of claim 14 wherein the surface comprises a conveyor belt.

16. The method of claim 15 wherein diamonds are removed from the conveyor belt as a function of their detected fluorescence.

17. The method of claim 16 wherein the diamonds are removed by a puffer or vacuum picker.

18. The method of claim 12 wherein the diamonds are colorless to near colorless.

19. The method of claim 12 wherein the short wavelength light includes light in the visible to UV range.

20. The method of claim 12 wherein the short wavelength light includes light in the blue to violet range.

* * * * *

UNITED STATES PATENT AND TRADEMARK OFFICE
CERTIFICATE OF CORRECTION

PATENT NO. : 8,514,377 B2  
APPLICATION NO. : 13/418122  
DATED : August 20, 2013  
INVENTOR(S) : Linares et al.

Page 1 of 1

It is certified that error appears in the above-identified patent and that said Letters Patent is hereby corrected as shown below:

Title page, in column 2, under "Other Publications", line 9, delete "Aliowance" and insert --Allowance--, therefor Title page, in column 2, under "Other Publications", line 9, delete "maiied" and insert --mailed--, therefor Title page, in column 2, under "Other Publications", line 11, delete "Filed" and insert --filed--, therefor Title page, in column 2, under "Other Publications", line 12, delete "Received" and insert --mailed--, therefor In the Drawings Sheet 1 of 2, Fig. 2, reference numeral 230, delete "FLUORESCING RED" and insert --FLUORESCE RED--, therefor In the Specification In column 1, line 31, delete "cvd" and insert --CVD--, therefor In column 1, line 38, delete "cvd" and insert --CVD--, therefor In column 1, line 54, delete "flow chart" and insert --flowchart--, therefor In column 2, line 47, delete "wave length" and insert --wavelength--, therefor In column 2, line 48, delete "wave length" and insert --wavelength--, therefor Signed and Sealed this  
Eleventh Day of November, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,514,377 B2 | |
| APPLICATION NO. | : 13/418122 | |
| DATED | : August 20, 2013 | |
| INVENTOR(S) | : Linares et al. | |

It is certified that error appears in the above-identified patent and that said Letters Patent is hereby corrected as shown below:

Title page, in the illustrative figure "FLUORESCING RED" should read --FLUORESCE RED--

Title page, in column 2, under "Other Publications", line 9, delete "Aliowance" and insert --Allowance--, therefor Title page, in column 2, under "Other Publications", line 9, delete "maiied" and insert --mailed--, therefor Title page, in column 2, under "Other Publications", line 11, delete "Filed" and insert --filed--, therefor Title page, in column 2, under "Other Publications", line 12, delete "Received" and insert --mailed--, therefor In the Drawings Sheet 1 of 2, Fig. 2, reference numeral 230, delete "FLUORESCING RED" and insert --FLUORESCE RED--, therefor In the Specification In column 1, line 31, delete "cvd" and insert --CVD--, therefor In column 1, line 38, delete "cvd" and insert --CVD--, therefor This certificate supersedes the Certificate of Correction issued November 11, 2014.

Signed and Sealed this
Ninth Day of December, 2014

Michelle K. Lee
*Deputy Director of the United States Patent and Trademark Office*

CERTIFICATE OF CORRECTION (continued)
U.S. Pat. No. 8,514,377 B2

In column 1, line 54, delete "flow chart" and insert --flowchart--, therefor

In column 2, line 47, delete "wave length" and insert --wavelength--, therefor

In column 2, line 48, delete "wave length" and insert --wavelength--, therefor